(12) United States Patent
Ladet

(10) Patent No.: US 9,375,699 B2
(45) Date of Patent: Jun. 28, 2016

(54) APPARATUS AND METHOD OF REACTING POLYMERS BY EXPOSURE TO UV RADIATION TO PRODUCE INJECTABLE MEDICAL DEVICES

(75) Inventor: Sébastien Ladet, Lyons (FR)

(73) Assignee: Sofradim Production, Trevoux (FR)

( * ) Notice: Subject to any disclaimer, the term of this patent is extended or adjusted under 35 U.S.C. 154(b) by 1056 days.

(21) Appl. No.: 13/202,345

(22) PCT Filed: Feb. 22, 2010

(86) PCT No.: PCT/IB2010/000639
§ 371 (c)(1),
(2), (4) Date: Nov. 3, 2011

(87) PCT Pub. No.: WO2010/095053
PCT Pub. Date: Aug. 26, 2010

(65) Prior Publication Data
US 2012/0041095 A1    Feb. 16, 2012

Related U.S. Application Data

(60) Provisional application No. 61/154,371, filed on Feb. 21, 2009.

(51) Int. Cl.
*A61B 17/00* (2006.01)
*B01J 19/12* (2006.01)

(52) U.S. Cl.
CPC ......... *B01J 19/123* (2013.01); *A61B 17/00491* (2013.01); *A61B 2017/00495* (2013.01); *B01J 2219/0888* (2013.01)

(58) Field of Classification Search
CPC ............... A61B 2017/00495; A61B 17/00491; B01J 19/123; B01J 2219/0088
See application file for complete search history.

(56) References Cited

U.S. PATENT DOCUMENTS

| 3,767,085 | A | 10/1973 | Cannon et al. |
| 4,326,532 | A | 4/1982 | Hammar |
| 4,359,049 | A | 11/1982 | Redl et al. |
| 4,464,321 | A | 8/1984 | Pittalis et al. |
| 4,538,920 | A | 9/1985 | Drake |
| 4,753,536 | A | 6/1988 | Spehar et al. |
| 4,839,345 | A | 6/1989 | Doi et al. |

(Continued)

FOREIGN PATENT DOCUMENTS

| BE | 1008260 A6 | 2/1996 |
| EP | 0490854 B1 | 9/1996 |

(Continued)

OTHER PUBLICATIONS

Q. Shi, et al., "The Immobilization of Proteins on Biodegradable Polymer Fibers via Click Chemistry", Biomaterials, 29, (2008), pp. 1118-1126.

(Continued)

*Primary Examiner* — Sanza McClendon

(57) ABSTRACT

Cross-linked compositions include a first precursor functionalized with a first reactive member and a second precursor functionalized with a second reactive member, the first and second reactive members covalently bonding with each other when exposed to UV radiation. The compositions are useful in a variety of surgical and wound treatment applications.

14 Claims, 2 Drawing Sheets

(56) References Cited

U.S. PATENT DOCUMENTS

| | | |
|---|---|---|
| 4,857,403 A | 8/1989 | De Lucca et al. |
| 4,880,662 A | 11/1989 | Habrich et al. |
| 5,021,207 A | 6/1991 | De Lucca et al. |
| 5,372,585 A | 12/1994 | Tiefenbrun et al. |
| 5,455,308 A | 10/1995 | Bastiaansen |
| 5,562,946 A | 10/1996 | Fofonoff et al. |
| 5,578,662 A | 11/1996 | Bennett et al. |
| 5,582,955 A | 12/1996 | Keana et al. |
| 5,612,050 A | 3/1997 | Rowe et al. |
| 5,797,679 A * | 8/1998 | Grulke et al. .................. 366/139 |
| 5,804,318 A | 9/1998 | Pinchuk et al. |
| 5,911,942 A | 6/1999 | Fofonoff et al. |
| 6,042,262 A * | 3/2000 | Hajianpour .................. 366/139 |
| 6,099,563 A | 8/2000 | Zhong |
| 6,107,365 A | 8/2000 | Bertozzi et al. |
| 6,107,453 A | 8/2000 | Zuccato et al. |
| 6,312,725 B1 | 11/2001 | Wallace et al. |
| 6,342,591 B1 | 1/2002 | Zamora et al. |
| 6,451,032 B1 | 9/2002 | Ory et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,624,245 B2 | 9/2003 | Wallace et al. |
| 6,881,766 B2 | 4/2005 | Hain |
| 6,958,212 B1 | 10/2005 | Hubbell et al. |
| 7,012,126 B2 | 3/2006 | Matsuda et al. |
| 7,105,629 B2 | 9/2006 | Matsuda et al. |
| 7,122,703 B2 | 10/2006 | Saxon et al. |
| 7,144,976 B2 | 12/2006 | Matsuda et al. |
| 7,172,877 B2 | 2/2007 | Ting |
| 7,247,692 B2 | 7/2007 | Laredo |
| 7,294,357 B2 | 11/2007 | Roby |
| 7,371,719 B2 | 5/2008 | Stupp et al. |
| 7,375,234 B2 | 5/2008 | Sharpless et al. |
| 7,560,588 B2 | 7/2009 | Breitenkamp et al. |
| 7,618,944 B2 | 11/2009 | Breitenkamp et al. |
| 7,638,558 B2 | 12/2009 | Breitenkamp et al. |
| 7,667,012 B2 | 2/2010 | Saxon et al. |
| 7,795,355 B2 | 9/2010 | Matyjaszewski et al. |
| 7,807,619 B2 | 10/2010 | Bertozzi et al. |
| 7,981,444 B2 | 7/2011 | Tomalia et al. |
| 7,985,424 B2 | 7/2011 | Tomalia et al. |
| 8,034,396 B2 | 10/2011 | Kapiamba et al. |
| 2002/0016003 A1 | 2/2002 | Saxon et al. |
| 2002/0161170 A1 | 10/2002 | Matsuda et al. |
| 2002/0169275 A1 | 11/2002 | Matsuda et al. |
| 2002/0173616 A1 | 11/2002 | Matsuda et al. |
| 2003/0100086 A1 | 5/2003 | Yao et al. |
| 2003/0135238 A1 | 7/2003 | Milbocker |
| 2003/0162903 A1 | 8/2003 | Day |
| 2003/0199084 A1 | 10/2003 | Saxon et al. |
| 2003/0205454 A1 | 11/2003 | Hlavinka et al. |
| 2004/0170752 A1 | 9/2004 | Luthra et al. |
| 2004/0185053 A1 | 9/2004 | Govindan |
| 2004/0209317 A1 | 10/2004 | Ting |
| 2004/0249438 A1 | 12/2004 | Lefranc et al. |
| 2005/0032081 A1 | 2/2005 | Ju et al. |
| 2005/0038472 A1 | 2/2005 | Furst |
| 2005/0148032 A1 | 7/2005 | Saxon et al. |
| 2005/0209601 A1 * | 9/2005 | Bowman et al. ................ 606/90 |
| 2005/0222427 A1 | 10/2005 | Sharpless et al. |
| 2005/0233389 A1 | 10/2005 | Ting et al. |
| 2005/0244453 A1 | 11/2005 | Stucke et al. |
| 2006/0018948 A1 | 1/2006 | Guire et al. |
| 2006/0036022 A1 | 2/2006 | Callaghan et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0142404 A1 | 6/2006 | Berge et al. |
| 2006/0147963 A1 | 7/2006 | Barone et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0212267 A1 | 9/2007 | Organ et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0021486 A1 * | 1/2008 | Oyola et al. .................. 606/169 |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0103564 A1 * | 5/2008 | Burkinshaw et al. ............ 607/96 |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2008/0317861 A1 | 12/2008 | Guan |
| 2009/0012457 A1 | 1/2009 | Childers et al. |
| 2009/0018646 A1 | 1/2009 | Zhao |
| 2009/0027603 A1 | 1/2009 | Samulski et al. |
| 2009/0038701 A1 | 2/2009 | Delmotte |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0099108 A1 | 4/2009 | Jones |
| 2009/0124534 A1 | 5/2009 | Reineke |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0203131 A1 | 8/2009 | Reineke et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | Mcanulty et al. |
| 2009/0269277 A1 | 10/2009 | Chang et al. |
| 2009/0281250 A1 | 11/2009 | Desimone et al. |
| 2009/0297609 A1 | 12/2009 | Shoichet et al. |
| 2009/0306310 A1 | 12/2009 | Wu et al. |

(56) References Cited

U.S. PATENT DOCUMENTS

| | | | |
|---|---|---|---|
| 2009/0312363 A1 | 12/2009 | Bradner et al. | |
| 2009/0325292 A1 | 12/2009 | Baker et al. | |
| 2010/0011472 A1 | 1/2010 | Hugel et al. | |
| 2010/0015046 A1 | 1/2010 | Govindan et al. | |
| 2010/0021391 A1 | 1/2010 | Douglas et al. | |
| 2010/0034862 A1 | 2/2010 | Laronde et al. | |
| 2010/0047258 A1 | 2/2010 | Wang et al. | |
| 2010/0048738 A1 | 2/2010 | Fleury et al. | |
| 2010/0069578 A1 | 3/2010 | Faust et al. | |
| 2010/0098640 A1 | 4/2010 | Cohen et al. | |
| 2010/0104589 A1 | 4/2010 | Govindan et al. | |
| 2010/0121022 A1 | 5/2010 | Musa et al. | |
| 2010/0159508 A1 | 6/2010 | Yang et al. | |
| 2010/0247433 A1 | 9/2010 | Tirrell et al. | |
| 2010/0286405 A1 | 11/2010 | Fokin et al. | |
| 2010/0291171 A1 | 11/2010 | Crescenzi et al. | |
| 2010/0303754 A1 | 12/2010 | Turpin et al. | |
| 2011/0008251 A1 | 1/2011 | Chang et al. | |
| 2011/0052696 A1 | 3/2011 | Hult et al. | |
| 2011/0060107 A1 | 3/2011 | Matyjaszewski et al. | |
| 2011/0143435 A1 | 6/2011 | Stayton et al. | |
| 2011/0177156 A1 | 7/2011 | Szoka, Jr. et al. | |
| 2012/0108695 A1* | 5/2012 | Won | B01F 7/04 522/3 |
| 2012/0220749 A1* | 8/2012 | Dasgupta | C08G 75/28 528/226 |

FOREIGN PATENT DOCUMENTS

| | | |
|---|---|---|
| EP | 1790702 A1 | 5/2007 |
| EP | 1795563 A1 | 6/2007 |
| EP | 1975230 A1 | 1/2008 |
| EP | 2014308 A2 | 1/2009 |
| EP | 2090592 A1 | 8/2009 |
| WO | WO 2006/012569 A1 | 2/2006 |
| WO | WO 2007/041394 A2 | 4/2007 |
| WO | WO 2007/121055 A1 | 10/2007 |
| WO | WO 2008/013618 A1 | 1/2008 |
| WO | WO 2008/075955 A2 | 6/2008 |
| WO | WO 2008/077406 A2 | 7/2008 |
| WO | WO 2008/108736 A1 | 9/2008 |
| WO | WO 2008/115694 A2 | 9/2008 |
| WO | WO 2008/120016 A1 | 10/2008 |
| WO | WO 2010/095049 A1 | 8/2010 |

OTHER PUBLICATIONS

Jérôme, et al., "Recent Advances in the Synthesis of Aliphatic Polyesters Ring-Opening Polymerization", Advanced Drug Delivery Reviews, 60, (2008), pp. 1056-1076.

Zhang, et al., "2-Azido-2-deoxycellulose: Synthesis and 1, 3-Dipolar Cycloaddition", Helvetica Chimica Acta, vol. 91, pp. 608-617 (2008).

Riva, et al., "Contribution of "Click Chemistry" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for Copper-Free Click Chemistry", J. Am. Chem. Soc., vol. 130, No. 34, (2008), pp. 11486-11493.

Sletten and Bertozzi, "A Hydrophilic Azacyclooctyne for Cu-free Click Chemistry", Org. Lett. (2008) 10(14), pp. 3097-3099.

Cazalis, et al., "C-Terminal Site-Specific PEGylation of a Truncated Thrombomodulin Mutant with Retention of Full Bioactivity, Bioconjugate Chem.", (2004), 15, pgs. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDévédec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self Assembling Materials", PNAS, 2002; 99(2), pp. 5133-5138.

Van Berkel, et al., "Metal-Free Triazole Formation as a Tool for Bioconjugation" Chem Bio Chem, 8, (2007), pp. 1504-1508.

Nottelet, et al., Synthesis of an X-ray opaque biodegradable copolyester by chemical modification of poly ($\in$-caprolactone) Biomaterials, 27, (2006), pp. 4943-4954.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Skierka, et al., "The Influence of Different Acids and Pepsin on the Extractability of Collagen From the Skin of Baltic Cod (Gadus morhua)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-O-cyanoalkylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-O-acetyl-1-thio-β-D-glucopyranose to 4-deoxy-1,2-O-isopropylident-L-$glycero$-pent-4-enopyranos-3-ulose-a convenient route to novel 4-deoxy-(1→5)-5-C-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of β-cyclodextrin with oligoethyleneamines", Biomaterials, 30, (2009), pp. 928-938.

Arora, et al., "A Novel domino-click approach for the synthesis of sugar based unsymmetrical bis-1,2,3- triazoles", Carbohydrate Research, 343, (2008), 139-144.

Chen, et al., "Synthesis of a $C_3$-symmetric (1→6)-N-acetyl-β-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, etal., "Effects of Trehalose Click Polymer Length on pDNA Complex Stability and Delivery Efficacy", Biomaterials, 28, (2007), pp. 2885-2898.

Godeau, et al., "Lipid-Conjugated Oligonucleotides via Click Chemistry" Efficiently Inhibit Hepatitis C Virus Translation, J. med. Chem., 2008, 51(15), pp. 2374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via $i$ to $i$ + 4 Intramolecular Side-chain to Side-chain Azide-Alkyne 1,3-Dipolar Cycloaddition" J. Org. Chem., 2008, 73 (15), pp. 5663-5614.

Dijk, et al., "Synthesis of Peptide-Based Polymers by Microwave-Assisted Cycloaddition Backbone Polymerization,"Biomacro molecules, 2007, 8(2), pp. 327-330.

Köster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.

(56) References Cited

OTHER PUBLICATIONS

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081.

Nandivada, et al. "Reactive polymer coatings that 'Click'.", Angewandte Chemie, International Edition 45, Apr. 2006, pp. 3360-3363.

Ossipov and Hilborn, "Poly(vinyl alcohol)-Based Hydrogels Formed by Click Chemistry", Macromelecules 2006, 39, pp. 1709-1718.

Binder and Sachsenhofer, "Click Chemistry in Polymer and Materials Science", Macromolecular Rapid Commun. 2007, 28, pp. 15-54.

* cited by examiner

APPARATUS AND METHOD OF REACTING POLYMERS BY EXPOSURE TO UV RADIATION TO PRODUCE INJECTABLE MEDICAL DEVICES

CROSS-REFERENCE TO RELATED APPLICATIONS

This application is a U.S. National Stage Application filed under 35 U.S.C. §371(a) of International Application No. PCT/IB2010/000639 filed Feb. 22, 2010, which claims the benefit of and priority to U.S. Provisional Application Ser. No. 61/154,371 filed Feb. 21, 2009, the entire contents of which are incorporated by reference herein.

BACKGROUND

1. Technical Field

The present disclosure relates to crosslinked compositions, for example of polymers, and more particularly to the use of click chemistry to form the crosslinked compositions, for example of polymers, using UV radiation, methods of preparing such compositions, for example of polymers, and medical devices made from or comprising such compositions, for example of polymers.

2. Background of Related Art

Click chemistry refers to a collection of reactions capable of forming a highly reliable molecular connection in solution or bulk state. Click chemistry reactions may be highly selective, high yield reactions which should not interfere with one another as well as other reactions.

It would be desirable to make an injectable medical device by mixing and dispensing first and second precursors functionalized for crosslinking by click chemistry using UV radiation for placement in situ.

SUMMARY

A first aspect of the present invention relates to a process of forming an injectable medical device comprising:
  mixing a volume of a first precursor functionalized with a first reactive member and a volume of a second precursor functionalized with a second reactive member, the first and second reactive members covalently bonding with each other when exposed to UV radiation into a mixing assembly; and
  exposing the mixed first and second precursors to UV radiation.

Another aspect of the present invention relates to a cross-linked composition obtained by:
  mixing a volume of a first precursor functionalized with a first reactive member and a volume of a second precursor functionalized with a second reactive member, the first and second reactive members covalently bonding with each other when exposed to UV radiation into a mixing assembly; and
  exposing the mixed first and second precursors to UV radiation.
  the first and second precursor each possess a core made of a biocompatible material.
  In embodiments, the first precursor and optionally the second precursor comprises a polyol core. The polyol may be selected from the group consisting of polyethers, polyesters, polyether-esters, polyalkanols, and combinations thereof.
  In embodiments, the first reactive member is a thiol group and the second reactive member is an alkene group.

Another aspect of the invention is a medical device comprising a cross-linked composition as above or obtained by the process above.

Another aspect of the invention is a cross-linked composition comprising a first precursor functionalized with a first reactive member and a second precursor functionalized with a second reactive member, the first and second reactive members covalently bonding with each other when exposed to UV radiation Another aspect of the invention is an apparatus comprising:
  a supply assembly configured to maintain and selectively dispense a first precursor functionalized with a first reactive member and a second precursor functionalized with a second reactive member, the first and second reactive members covalently bonding with each other when exposed to UV radiation.
  a mixing assembly configured to mix the first and second precursors in a mixing cavity; and
  at least one source of UV radiation positioned to irradiate the mixed first and second precursors.

The present disclosure relates to an apparatus and process for forming medical devices from one or more injectable compositions. The apparatus includes a supply assembly configured to maintain and selective dispense a first precursor and a second precursor, a mixing assembly configured to mix the first and second precursors in a mixing cavity, and at least one catalyzing element extending longitudinally through the mixing cavity. The catalyzing element includes a source of UV radiation to aid in the cross-linking of the first and second precursors. The process includes dispensing a volume of the first precursor and a volume of the second precursor into a mixing assembly and mixing the first and second precursors. The first and second precursors each possess a core and at least one functional group known to have click reactivity with each other when exposed to UV radiation. The mixed precursors are irradiated with UV light to produce a composition for use as a medical device.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF THE EMBODIMENTS

Figure 1:
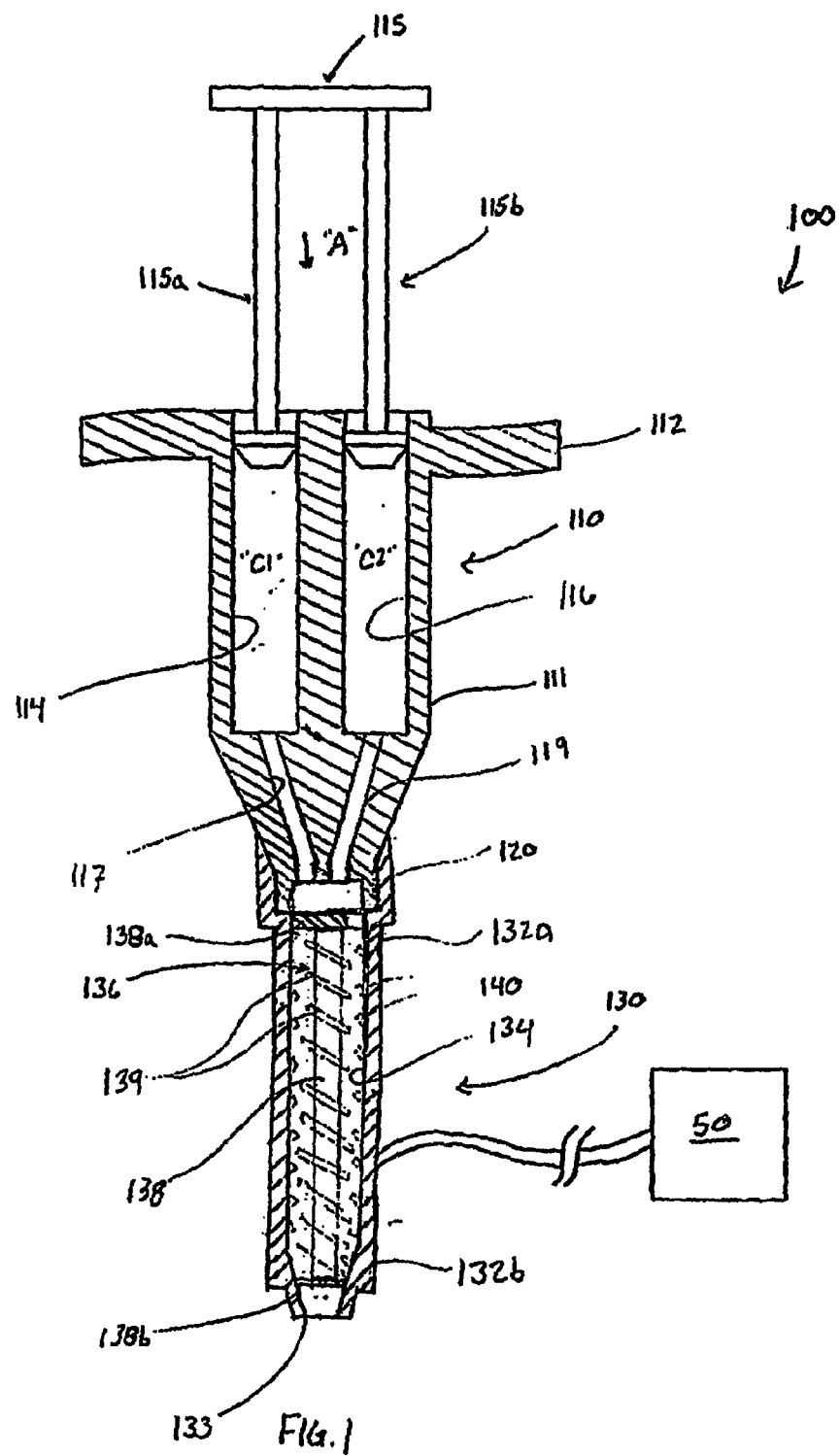
FIG. 1 is a cross-sectional view of an apparatus for mixing and catalyzing first and second precursors to form medical devices in accordance with the present disclosure.

Cross-linked compositions in accordance with the present disclosure include a first precursor functionalized with a first reactive member and a second precursor functionalized with a second reactive member, the first and second reactive members covalently bonding with each other when exposed to UV radiation.

In the present application, unless otherwise specified, the expressions 'functional group", "functional unit", "functionality", "functional group known to have click reactivity" and "reactive member" in relation to the first and second precursors are used interchangeably to designate a functional group known to have click reactivity, in particular when exposed to UV radiation.

The compositions are useful in a variety of surgical and wound treatment applications. The first and second precursors may each possess a core functionalized with a reactive member.

The Core Component

The core of the first and second precursors may be any suitable biocompatible material. In embodiments, the first and second precursors may be different materials, thus forming copolymer cross-linked compositions. The cross-linked compositions may be formed from a natural material or a synthetic material. The material from which the cross-linked compositions are formed may be bioabsorbable or non-bioabsorbable. It should of course be understood that any combination of natural, synthetic, bioabsorbable and non-bioabsorbable materials may be used to form the cross-linked compositions. Such cores may thus be linear, branched, star-shaped, dendrimeric, and the like.

In embodiments, suitable cores for use as the first and second precursors may be prepared from a polyol, a polyamine, or a polythiol. In embodiments a polyol may be used to form a core. Examples of such polyols include, in embodiments, polyethers, polyesters, polyether-esters, polyalkanols, combinations thereof, and the like.

Suitable polyethers which may be utilized in forming the core of the first precursor and/or the second precursor are within the purview of those skilled in the art and include, for example, poly(alkylene glycols), such as poly(ethylene glycol), poly(propylene glycol), poly(butylene glycol), poly(tetramethylene glycol), poly(hexamethylene glycol), copolymers such as cyclodextrin-poly(alkylene glycols), polyacetals, and combinations thereof. In embodiments a suitable polyether may include poly(ethylene glycol).

Suitable polyesters which may be utilized in forming the core of the first precursor and/or the second precursor are within the purview of those skilled in the art and include, for example, trimethylene carbonate, ε-caprolactone, p-dioxanone, glycolide, lactide, 1,5-dioxepan-2-one, poly(butylene adipate), poly(ethylene adipate), poly(ethylene terephthalate), dipoly(ethylene glycol) adipate and combinations thereof.

In addition, as noted above, the first precursor and/or the second precursor may include a poly(ether-ester) block. Any suitable poly(ether-ester) block within the purview of those skilled in the art may be utilized. These macromers may include an aliphatic diacid, aromatic diacid, alicyclic diacid, or combinations thereof, linking two dihydroxy compounds (sometimes referred to herein as a "poly(ether-ester) macromer"). Up to ten repeats of the poly(ether-ester) macromer may be present.

Suitable diacids which may be utilized in forming the poly(ether-ester) macromer include, for example, diacids having from about 2 to about 10 carbon atoms. Suitable diacids include, but are not limited to, sebacic acid, azelaic acid, suberic acid, pimelic acid, adipic acid, glutaric acid, succinic acid, malonic acid, oxalic acid, terephthalic acid, cyclohexane dicarboxylic acid, and combinations thereof.

Suitable dihydroxy compounds which may be utilized in forming the poly(ether-ester) macromer include, for example, polyols including polyalkylene oxides, polyvinyl alcohols, polycaprolactone diols, and the like. In some embodiments, the dihydroxy compounds can be a polyalkylene oxide such as polyethylene oxide ("PEO"), polypropylene oxide ("PPO"), block or random copolymers of polyethylene oxide (PEO) and polypropylene oxide (PPO), and combinations thereof.

In one embodiment, a polyethylene glycol ("PEG") may be utilized as the dihydroxy compound. It may be desirable to utilize a PEG with a molecular weight of from about 200 g/mol to about 10000 g/mol, in embodiments from about 400 g/mol to about 900 g/mol. Suitable PEGs include those commercially available from a variety of sources under the designations PEG 200, PEG 400, PEG 600 and PEG 900.

Any method may be used to form the poly(ether-ester) macromer. In some embodiments, the poly(ether-ester) macromer may be formed by combining adipoyl chloride with a PEG such as PEG 600 and pyridine in a suitable solvent, such as tetrahydrofuran (THF). The solution may be held at a suitable temperature, from about −70° C. to about 25° C., for a period of time of from about 4 hours to about 18 hours, after which the reaction mixture may be filtered to remove the precipitated pyridine hydrochloride by-product and the resulting poly(ether-ester) macromer, here a PEG/adipate compound. The resulting poly(ether-ester) macromer may be obtained from the solution by the addition of an ether or petroleum ether, and collected by suitable means which can include filtration. Other methods suitable for producing such macromers are within the purview of those skilled in the art.

In embodiments, components utilized in forming poly (ether-esters) may be functionalized and reacted to form poly (ether-ester-urethanes), poly(ether-ester-ureas), and the like.

Other examples of suitable poly(ether-ester) blocks which may be utilized include, but are not limited to, polyethylene glycol-polycaprolactone, polyethylene glycol-polylactide, polyethylene glycol-polyglycolide, and various combinations of the individual polyethers and polyesters described herein. Additional examples of suitable poly(ether-ester) blocks include those disclosed in U.S. Pat. No. 5,578,662 and U.S. Patent Application No. 2003/0135238, the entire disclosures of each of which are incorporated by reference herein.

In embodiments, the resulting poly(ether-ester) macromer may be of the following formula:

$$\text{HO}-(\text{X-A})_y\text{-X}-\text{OH} \quad \quad (I)$$

wherein A is a group derived from an aliphatic, aromatic, or alicyclic diacid; X can be the same or different at each occurrence and may include a group derived from a dihydroxy compound; and y may be from about 1 to about 10. In some embodiments, the A group can be derived from adipic acid, and X can be derived from a polyethylene glycol having a molecular weight of from about 200 g/mol to about 1000 g/mol, in embodiments from about 400 g/mol to about 800 g/mol, in embodiments about 600 g/mol.

The molecular weight and viscosity of these compounds may depend on a number of factors such as the particular diacid used, the particular dihydroxy compound used, and the number of repeat units present. Generally, the viscosity of these compounds may be from about 300 to about 10,000 cP at 25° C. and a shear rate of 20.25 sec$^{-1}$.

In other embodiments, polyrotaxanes may be utilized as the core of the first precursor and/or the second precursor. Polyrotaxane materials include cyclic molecules, linear molecules threaded through the cyclic molecules, and optionally bulky end groups on the linear molecules to prevent the loss of the cyclic molecules by dethreading. With respect to rotaxanes, "linear molecules" refers to any suitable molecules, whether branched or unbranched, that are capable of threading the cyclic molecules to form the rotaxane material. The linear molecules are generally in the form of chains that are unbranched. Branching of the linear molecules may occur, but not to the extent that the branching significantly interferes with the formation of the rotaxane material.

Examples of suitable polyrotaxanes include those created by linear polymers such as poly(ethylene oxide) (PEO) penetrating the inner cavity of cyclodextrins (CDs) to form inclusion complexes with a necklace-like supramolecular structure.

In addition to the polyols described above, in embodiments a polyamine and/or a polythiol may be used to form a core of first and second precursors herein.

In embodiments, the polyol, such as a polyether, polyester, or polyether-ester as described above, may be a branched polyol. Such a polyol may have a central core from which from about 3 to about 12 arms may extend, with hydroxyl groups at the free terminal of each arm. In embodiments, the polyol, such as a polyether, polyester, or polyether-ester as described above, may be endcapped with functional groups.

The Reactive Members

The first precursor and the second precursor each have at least one reactive member known to have click reactivity when exposed to UV radiation. In embodiments, the precursors may have from about 2 to about 50 reactive members. The click chemistry reaction of the present disclosure includes first and second precursors each having terminal and/or side chain functionality. The first and second precursors are functionalized by converting an attached functional unit on the precursor thereby providing site specific functional materials, site specific functional materials comprising additional functionality, or chain extended functional materials. Optionally, a linker may or may not be present for linking a functional group to the precursor. These reactive members may form arms extending from the core(s). Such cores may thus be linear, branched, star-shaped, dendrimeric, and the like.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

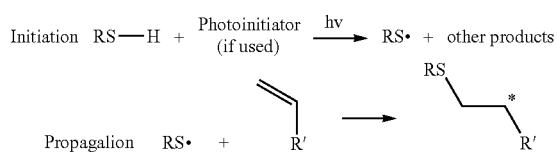

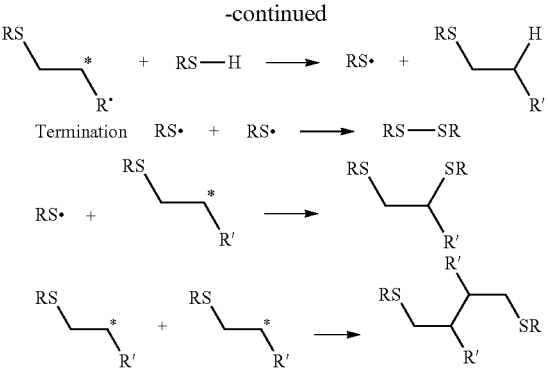

The thiol moieties may be selected from any suitable compound having a sulfur atom and a hydrogen atom (—SH). Alkene or olefin moieties may be selected from any suitable compound having a carbon double bond (C=C).

In embodiments, the first precursor may be functionalized with at least two thiol groups and the second precursor may be functionalized with at least two alkene groups. Where one of the precursor is functionalized with two groups, the other precursor may be functionalized with 3 or more groups.

In preparing compositions in accordance with the present disclosure, the first and second precursors may be commercially available pre-functionalized cores or may be synthesized. For example, thiolated macromers, such as polyethylene glycol dithiol, are commercially available.

The core of the first and second precursor can be provided with click reactive members using any variety of suitable chemical processes.

For example, the monomers from which the core is made can be functionalized so that the reactive members appear along the length of the core. In such embodiments, monomers can be initially functionalized with a group such as a halogen to provide a reactive site at which the desired first click reactive member can be attached after polymerization. Thus, for example, a cyclic lactone (e.g., glycolide, lactide, caprolactone, etc.) can be halogenated and then polymerized using known techniques for ring opening polymerization. Once polymerized, the halogenated sites along the resulting polyester chain can be functionalized with a click reactive member, for example, by converting pendant chlorides on the core into thiol. Other methods for functionalizing lactones are described in Jérôme et al., *Advanced Drug Delivery Reviews*, 60, pages 1056-1076 (2008) and Shi et al., *Biomaterials*, 29, pages 1118-1126 (2008). The entire disclosure of each of these articles is incorporated herein by this reference.

Moreover, thiols may be prepared by the esterification of an appropriate halogen-containing polyol with mercaptocarboxylic acid in the presence of an acid catalyst, the water formed during the reaction being removed as an azeotrope in a suitable solvent. The reaction is carried out at atmospheric pressure at a temperature in the range of from 60° C. to about 150° C., in embodiments from about 60° C. to about 110° C., for a period of about 30 minutes to about 24 hours.

Suitable acid catalysts include, but are not limited to, p-toluenesulfonic acid, sulfuric acid, hydrochloric acid and the like. Useful inert solvents include but are not limited to saturated aliphatic hydrocarbons, aromatic hydrocarbons, chlorinated hydrocarbons, ethers, ketones, etc. Representative nonlimiting examples of solvents include toluene, benzene, xylene, chloroform, 1,2-dichloroethane, etc.

Those skilled in the art reading this disclosure will readily envision chemical reactions for activating other core materials to render them suitable for use as precursors in the presently described methods.

Formulating the Compositions

In preparing the injectable composition in accordance with the present disclosure, the first and second precursors may take the form of any solution, suspension, semi-solid, or solid material capable of allowing the two components to interact and crosslink. The first and second precursors may be in granular, pellet, or powder form, or alternatively, may be in solution. Suitable solvents which may be utilized to form a dilute solution include any biocompatible solvent within the purview of those skilled in the art which will not interfere with the reaction of the reactive members of the first and second precursors. Suitable solvents which may be utilized include, for example, polar solvents such as water, ethanol, triethylene glycol, dimethyl sulfoxide, glymes (such as diglyme, triglyme, tetraglyme, and the like), poly(ethylene glycols), methoxy-poly(ethylene glycols), dimethylformamide, dimethylacetamide, gamma-butyrolactone, n-methylpyrrolidone, ketones such as methyl ethyl ketone, cyclohexanone, diethylene glycol momethyl ether acetate, diethylene glycol monobutyl ether acetate, diethylene glycol monomethyl ether, diethylene glycol monoethyl ether, diethylene glycol monobutyl ether, diethylene glycol monoisobutyl either, diisobutyl ketone, diacetone alcohol, ethyl amyl ketone, ethyl lactate, and the like. In other embodiments, solvents such as tetrahydrofuran, ethyl acetate, isopropyl acetate, butyl acetate, isopropanol, butanol, acetone, and the like, may be utilized. In embodiments, combinations of any of the foregoing solvents may be utilized to form a dilute solution. The amount of solvent used will depend on a number of factors, including the particular first precursor, second precursor, or combination thereof that are to be employed and the intended end use of the composition.

The rate of cross-linking of the first and second precursors of the present disclosure may be tailored by controlling the concentration of the first precursor and the second precursor. Generally, a faster cross-linking time may be observed at a higher concentration of either the first or second precursors than the rate observed for the same components at a lower concentration. In embodiments, the ratio of first precursor reactive members to second precursor reactive members is from about 1:2 to about 1:1. Alternatively, the rate of cross-linking may be adjusted by varying the UV intensity or time of exposure.

Initiation of polymerization is accomplished by irradiation with light at a wavelength of between about 20-400 nm, in the ultraviolet range. The UV radiation may be obtained from sunlight or special lamps or light sources which emit UV light having a wavelength in the range above. Particularly, thiolene polymerizations are photochemically initiated, step growth, free-radical processes that take place between thiols and alkenes via a sequential propagation/chain-transfer process. Thiol-ene systems form ground state charge transfer complexes, and therefore photopolymerize even in the absence of initiators in reasonable polymerization times. Since the complex which absorbs the light is consumed by the polymerization, the polymer itself does not absorb light. Where the fiber is opaque, UV irradiation will provide only surface cross-linking. Where the fiber is transparent or translucent (e.g., while still molten or in solution), exposure to UV radiation may result in bulk cross-linking.

The injectable composition may optionally be formulated to achieve delivery of a bioactive agent. Thus, in some embodiments, at least one bioactive agent may be combined with either the first precursor or the second precursor, introduced separately through the supply assembly, and/or may be separately applied to finished medical device. The agents may be freely admixed with the precursors (making sure not reactive with them) or may be tethered to the precursors through any variety of chemical bonds. In these embodiments, the present injectable composition can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. Some examples of these agents include, but are not limited to hydrophilic polymers such as poly(vinyl pyrrolidone), carboxymethyl cellulose, alginates, hyaluronic acid, poly(ethylene oxide), poly(vinyl alcohols), and combinations thereof.

Suitable antimicrobial agents which may be included as a bioactive agent of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in accordance with the present disclosure include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

The Dispensing Apparatus

With reference now to the figures, embodiments of an apparatus for mixing and catalyzing a mixture composed of two or more components or precursors herein will be described. Like reference numerals will refer to similar structure throughout the embodiments. The term "proximal" will be used in the traditional sense as being the portion of the element that is closest to the user, while "distal" will refer to the portion of the element that is furthest from the user.

Referring initially to FIG. 1, an apparatus according to an embodiment of the present disclosure is shown generally as mixing applicator 100. Applicator 100 includes a supply assembly 110 and a mixing assembly 130 operably connected to supply assembly 110. Supply assembly 110 is configured to maintain and selectively dispense a first and second component to mixing assembly 130. Mixing assembly 110 is configured to mix the first and second component and catalyze the resulting mixture.

Still referring to FIG. 1, as shown, supply assembly 110 includes a housing 111 configured for operable hand-held engagement by a user. Housing 111 includes a flange member 112 formed on a proximal end for facilitating engagement by a user and an extension 120 formed on a distal end for selectively positioning mixing assembly 130 relative to a target site. In one embodiment, extension 120 is of a sufficient length to position a distal end of mixing assembly 130 within the body cavity of a patient while maintaining supply assembly 110 outside of the body. In this manner, extension 120 may include a wire or other element (not shown) for maintaining extension 120 in a flexed or bent condition. Housing 111 further includes first and second component chambers 114, 116 configured to receive a first and second component "C1", "C2", respectively. A plunger assembly 115, including first and second plunger members 115a, 115b, operably engages housing 111 and is configured for selectively dispensing first and second components "C1", "C2" from first and second component chambers 114, 116, respectively, in a syringe-like manner.

Housing 111 further includes first and second component conduits 117, 119 that fluidly communicate first and second component chambers 114, 116, respectively, with mixing assembly 130. First and second component conduits 117, 119 extend distally from first and second chambers 114, 116, respectively, through extension 120 of housing 111. In an alternative embodiment, first and second component conduits 117, 119 may form a single conduit to permit mixing of first and second components "C1", "C2" prior to reaching mixing cavity 134.

Although shown as a hand-held apparatus capable of dispensing only two components, it is envisioned that the aspects of the present disclosure may be adapted for use with any known supply assembly capable of selectively dispensing two or more components. Alternative supply assemblies may be configured to dispense more than two components, remotely dispense the components, i.e., from a cart mounted supply assembly via a conduit or other tubing, and/or dispense the components at different rates to produce mixtures composed of different percentages of the components.

Still referring to FIG. 1, mixing assembly 130 includes a substantially elongate member 132 including an open proximal end 132a, a substantially closed distal end 132b, and defining a mixing cavity 134 therebetween. Proximal end 132a of elongate member 132 is configured for operable engagement with extension 120 of housing 111. Proximal end 132a may be configured for frictional engagement with extension 120, as shown, or may instead be configured for mechanical fastening to extension 120, such as with a bayonet coupling, snap-fit fitting or threading. Mixing assembly 130 engages extension 120 such that mixing cavity 134 is maintained in fluid communication with first and second chambers 114, 116 of housing 111 via first and second conduits 117, 119. Distal end 132b of mixing assembly 130 defines an opening or outlet 133 configured for dispensing the mixture of first and second components "C1", "C2" from mixing cavity 130. Depending on the mixture and/or the desired method of application, outlet 133 may include a single bore, as shown, or may instead include multiple openings, a spray tip, a needle tip and/or any other suitable configuration.

With reference still to FIG. 1, mixing assembly 130 further includes an elongated mixing/catalyzing elements 136. Mixing element 136 extends longitudinally through mixing cavity 134 and includes a lamp or bulb 138. In one embodiment, mixing element 136 extends substantially the entire length of mixing cavity 134. Lamp 138 is supported on a proximal and distal end by supports 138a, 138b. Supports 138a, 138b are configured to maintain lamp 138 within mixing cavity 134 while permitting first and second components "C1", "C2", and a mixture thereof, to flow through mixing cavity 134. Lamp 138 may include any suitable lamp or bulb capable of emitting one or more catalyzing lights, e.g. ultraviolet. In one embodiment, lamp 138 may include multiple lamps or bulbs. Lamp 138 is operably connected to a power source 50. Power source 50 may include any suitable source of energy for powering lamp 138. Although shown remotely connected to power source 50, it is envisioned that power source 50 may be integrally formed with applicator 100. Power source 50 may be manually activated. Alternatively, applicator 100 may include a sensor or other suitable device (not shown) for activating power source 50 upon depression of plunger assembly 115.

Mixing element 136 further includes blades 139 extending radially outward along the length of lamp 138. Blades 139 may be integrally formed with lamp 138, or may instead be securely affixed or selectively formed on lamp 138. Blades 139 are configured to mix first and second components "C1", "C2" as they traverse mixing cavity 134. The size, construction and spacing of blades 139 may be varied depending the composition of the components being mixed as well as the composition of the resulting mixture. Mixing assembly 130 may further include protrusions 140 extending radially into mixing cavity 134. Protrusions 140 are configured to assist in the mixing of first and second components "C1", "C2" and to cause the resulting mixture to swirl through mixing cavity 134. In this manner, more of the resulting mixture is exposed to lamp 138 and the light being emitted therefrom. In one embodiment, mixing cavity 134 may be coated with a material capable of reflecting the light from lamp 138 back into mixing cavity 134 to maximize the effect of the light.

The operation of applicator 100 will now be described with reference to FIG. 1. Initially, a first and second component "C1", "C2" are received within first and second component chambers 114, 116, respectively, and plunger assembly 115 is operably engaged with housing 111. Prior to or following the addition of first and second components "C1", "C2" to housing 111, mixing assembly 130 is operably connected to extension 120 of housing 111. In this manner, applicator 100 is ready for use.

By depressing plunger assembly 115, in the direction of arrow "A", first and second components "C1", "C2" are dispensed from first and second chambers 114, 116, respectively, through respective first and second component conduits 117, 119. Initial mixing of first and second components "C1", "C2" occur as first and second components exit first and second component conduits 117, 119. As initially mixed first and second components "C1", "C2" flow through mixing cavity 134, first and second components "C1", "C2" are further mixed as the components contact blades 139 and protrusions 140. The resulting mixture is exposed to the light being emitted from lamp 138. Contact of the mixture with blades 139 and protrusions 140 ensures that more of the mixture is exposed to the catalyzing light. The length of mixing assembly 130 and/or the rate through which the mixture flows therethrough may vary depending on the desired exposure time of the mixture to the light. Continued depression of plunger assembly 115 causes the release of the resulting catalyzed mixture from outlet 133 of mixing assembly 130. As detailed above, outlet 133 may include various configurations, depending on the mixture being dispensed and the desired method of application.

Figure 2:
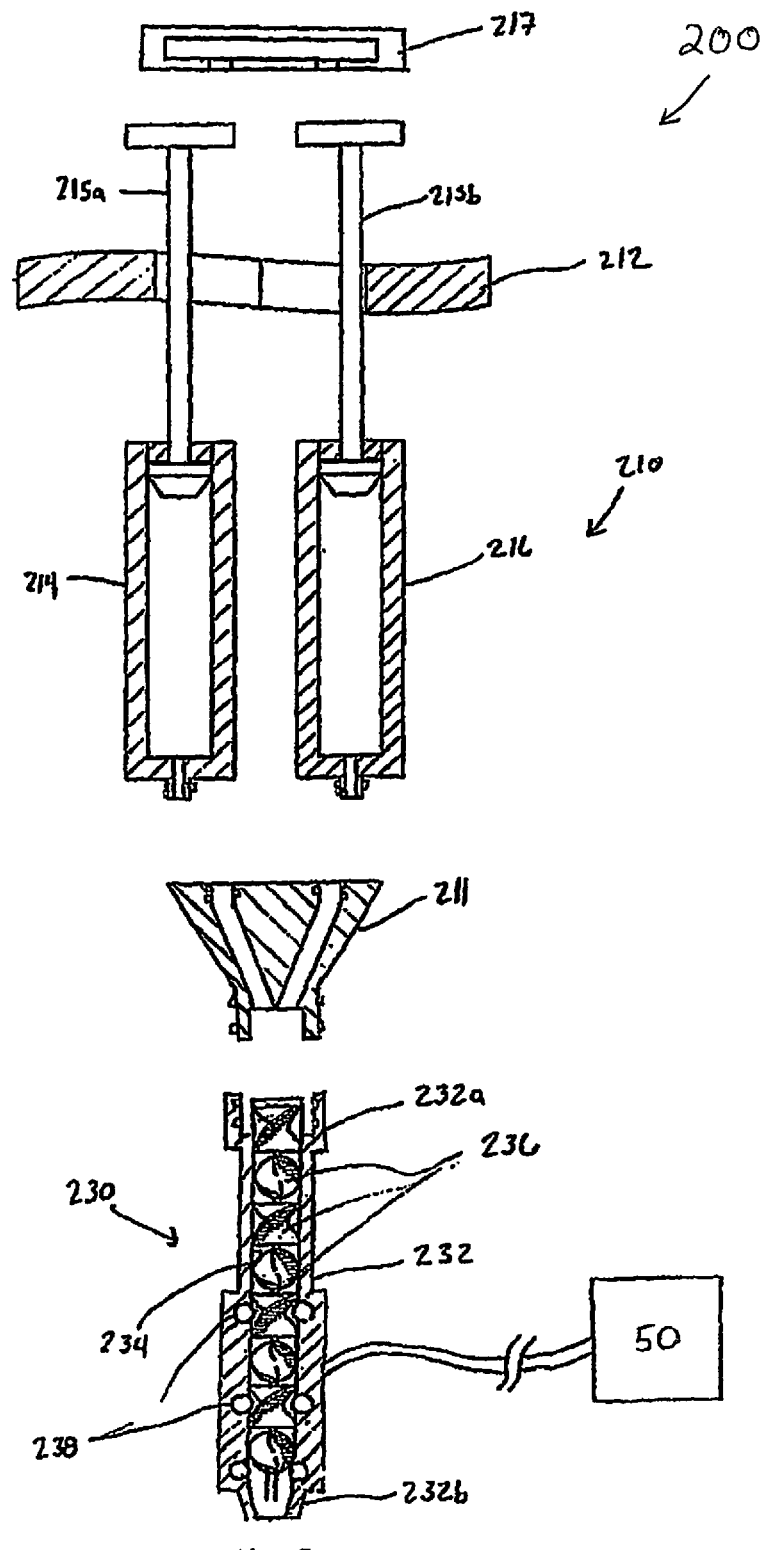
FIG. 2 is a cross-sectional view of an alternative embodiment of an apparatus for mixing and catalyzing first and second precursors to form medical devices in accordance with the present disclosure.

With reference now to FIG. 2, an alternative embodiment of the present disclosure is shown generally as applicator 200. Applicator 200 is substantially similar to applicator 100 and will therefore only be described as relates to the differences therebetween. Supply assembly 210 includes first and second component syringes 214, 216 operably connectable to a housing 211. First and second component syringes 214, 216 are operably connectable by a flange member 212 and each include a first and second plunger members 215a, 215b, respectively, for selectively dispensing respective first and second components "C1", "C2" therefrom. Supply assembly 210 further includes a plunger cap member 217 configured to fit about an end of first and second plunger member 215a, 215b. In this manner, first and second plunger members 215a, 215b may be depressed uniformly, thereby dispensing equal amounts of first and second components "C1", "C2" from respective first and second component syringes 214, 216.

With reference still to FIG. 2, mixing assembly 230 includes an elongate member 232 having substantially open proximal end 232a, a substantially closed distal end 232b, and a mixing cavity 234 extending therebetween. Proximal end 232a of mixing assembly 230 includes a snap fitting for operable connection with housing 211. Mixing assembly 230 further includes a plurality of mixing elements 236 extending the length of mixing cavity 234. Mixing elements 236 may form substantially helical members, as shown, or may instead include multiple planar or curved blades, a single helical screw or any other suitable configuration for mixing first and second components "C1", "C2". As shown, mixing elements 236 are arranged in an alternating orientation to increase the turbulence of first and second components "C1", "C2" as the components flow through mixing cavity 234. Mounted within elongate member 232 and extending along at least a portion of mixing cavity 234 are lamps 238. Lamps 238 define substantially annular lamp members capable of emitting a catalyzing light into mixing cavity 134. Mixing assembly 230 may include one or more lamps 238. Lamps 238 may be configured to emit the same or different catalyzing light. The spacing, number and size of lamps 238 may be varied depending on the characteristics of the components being mixed and the resulting mixture. Lamps 238 are operably connected to a power source 50.

UV lamps suitable for use in the present disclosure are well known to those skilled in the art. Typically, the UV energy is provided by causing a discharge in a gaseous medium contained in a UV transmissive bulb or envelope. Typical gas fillings include mixtures of argon (and/or other gases such as xenon XE, krypton KR) and mercury which, upon discharge therein, is rich in ultraviolet (other UV rich gases on ionization may be used). Typically, a ballast power supply is connected to the electrodes. In electronic ballast systems, a step-up transformer provides a high striking or ionization voltage, several hundred volts (which, once the lamps are energized, is lowered to a normal operating voltage (normally in the range of 100-200 volts)).

Use of the Compositions

The injectable compositions of the present disclosure can be used for a number of different human and animal medical applications including, but not limited to, wound closure (including surgical incisions and other wounds), sealants, adhesion barriers, and other implantable devices. Adhesives may be used to bind tissue together either as a replacement of, or as a supplement to, sutures, staples, clamps, tapes, bandages, and the like. Use of the present compositions can eliminate or substantially reduce the number of sutures normally required during current practices, and eliminate the subsequent need for removal of staples and certain types of sutures. The compositions described herein can thus be suitable for use with delicate tissues where sutures, clamps or other conventional tissue closure mechanisms may cause further tissue damage. For example, the compositions of the present disclosure may be used to seal or adhere delicate tissue together in place of conventional tools that may cause mechanical stress. The present compositions can also be used to seal air and/or fluid leaks in tissue as well as to prevent post-surgical adhesions and to fill voids and/or defects in tissue.

For example, to effectuate the joining of two tissue edges, the two edges may be approximated, and an injectable composition of the present disclosure may be applied to the two approximated edges with a mixing applicator as described above. A second tissue surface may then be contacted with the tissue possessing the composition so that it adheres thereto.

The compositions described herein can also be used as sealants. When used as a sealant, a composition of the present disclosure can be used in surgery to prevent or inhibit bleeding or fluid leakage both during and after a surgical procedure.

It can also be applied to prevent air leaks associated with pulmonary surgery. Compositions herein may be applied directly to the desired area in at least an amount sufficient to seal off any defect in the tissue and seal off any fluid or air movement. The compositions may also be used to prevent or control blood or other fluid leaks at suture or staple lines.

The composition of the present disclosure crosslinks rapidly, in embodiments, in less than one minute. Compositions of the present disclosure can thus be applied to the wound and allowed to set, thereby closing the wound.

The present compositions also can be used to attach skin grafts and position tissue flaps during reconstructive surgery. Alternatively, the present compositions can be used to close tissue flaps in periodontal surgery.

In another embodiment, the present disclosure is directed to a method for using compositions of the present disclosure to adhere a medical device to tissue. Suitable medical devices include implants. Other medical devices include, but are not limited to, pacemakers, stents, shunts and the like. Generally, for adhering a device to the surface of animal tissue, a composition of the present disclosure can be applied to the device, to the tissue surface or to both. The device and tissue surface are then brought into contact with the present composition therebetween. In other embodiments the first component may be applied to the device or tissue surface, and the second component applied to the other. The device and tissue surface are brought into contact with each other, so that the first component and second component are in contact with each other. Application of the catalyst will result in formation of a composition of the present disclosure. Once the composition crosslinks and sets, the device and tissue surface are effectively adhered to each other.

The present compositions can also be used to prevent post surgical adhesions. In such an application, a composition of the present disclosure may be applied and cured to form a layer on surfaces of internal tissues in order to prevent the formation of adhesions at a surgical site during the healing process.

The resulting injectable compositions have a number of advantageous properties. The compositions of the present disclosure are safe, possess enhanced adherence to tissue, are biodegradable, have enhanced hemostatic potential, have low cost, and are easy to prepare and use. By varying the selection of the compounds utilized to form the composition, the strength and elasticity of the composition can be controlled, as can the gelation time.

Adhesives and/or sealants formed with compositions of the present disclosure possess excellent strength and similar physical properties. The compositions herein rapidly form a compliant gel matrix, which insures stationary positioning of tissue edges or implanted medical devices in the desired location and lowers overall required surgical/application time. The composition forms strong cohesive bonds. It exhibits excellent mechanical performance and strength, while retaining the necessary pliability to adhere living tissue. This strength and pliability allows a degree of movement of tissue without shifting the surgical tissue edge.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, although the mixing elements herein described are static within the mixing cavity, it is envisioned that the mixing elements may be operably connected to a motor, thereby permitting movement of the mixing elements.

What is claimed is:

1. An apparatus comprising:
   a supply assembly configured to maintain and selectively dispense a first precursor functionalized with a first click reactive member and a second precursor functionalized with a second click reactive member, the first and second click reactive members capable of covalently bonding with each other
   a mixing assembly configured to mix the first and second precursors in a mixing cavity, and,
   at least one source of UV radiation positioned to irradiate the mixed first and second precursors within the mixing assembly, wherein the at least one source of UV radiation comprises a mixing element comprising a lamp which extends longitudinally through the mixing assembly and the mixing element further includes blades extending radially outward along a length of the lamp.

2. The apparatus of claim 1 wherein the mixing element extends an entire length of the mixing cavity.

3. The apparatus of claim 2 wherein the lamp is supported on a proximal and distal end by supports configured to maintain the lamp within the mixing cavity while per ing the first and second precursors through the mixing cavity.

4. The apparatus of claim 1 wherein the mixing assembly further comprises a coating on at least a portion thereof, the coating comprising a material capable of reflecting UV radiation from the at least one source of UV radiation within the mixing assembly.

5. The apparatus of claim 1 wherein the mixing assembly comprises an elongate member having a proximal end and a distal end with the mixing cavity extending therebetween.

6. An apparatus comprising:
   a supply assembly configured to maintain and selectively dispense a first precursor functionalized with a first click reactive member and a second precursor functionalized with a second click reactive member, the first and second click reactive members capable of covalently bonding with each other,
   a mixing assembly comprising an elongate member having a proximal end, a distal end and a mixing cavity extending therebetween, the mixing assembly configured to mix the first and second precursors in the mixing cavity, and
   a source of UV radiation positioned to irradiate the mixed first and second precursors within the mixing assembly, wherein the source of UV radiation comprises a plurality of lamps mounted within the elongate member and extending along at least a portion of the mixing cavity.

7. The apparatus of claim 6 further comprising a plurality of mixing elements which form substantially helical members.

8. The apparatus of claim 7 wherein the plurality of mixing elements are arranged in an alternating orientation.

9. The apparatus of claim 1, wherein the first and second precursor each possess a core made of a biocompatible material.

10. The apparatus of claim 1, wherein the first precursor and optionally the second precursor comprises a polyol core.

11. The apparatus of claim 10, wherein the polyol is selected from the group consisting of polyethers, polyesters, polyether-esters, polyalkanols, and combinations thereof.

12. The apparatus of claim 1, wherein the first click reactive member is a thiol group and the second click reactive member is an alkene group.

13. The apparatus of claim 1, wherein the mixing assembly further comprises protrusions extending radially into the mixing cavity to assist in the mixing of first and second precursors.

14. The apparatus of claim 6, wherein the lamps comprise an annular configuration.

* * * * *